United States Patent [19]

Verheyden et al.

[11] 4,423,050

[45] * Dec. 27, 1983

[54] 9-(1,3-DIHYDROXY-2-PROPOXYMETHYL)-GUANINE AS ANTIVIRAL AGENT

[75] Inventors: Julien P. H. Verheyden, Los Altos; John C. Martin, Redwood City, both of Calif.

[73] Assignee: Syntex (U.S.A.) Inc., Palo Alto, Calif.

[ * ] Notice: The portion of the term of this patent subsequent to Oct. 19, 1999, has been disclaimed.

[21] Appl. No.: 380,969

[22] Filed: May 24, 1982

Related U.S. Application Data

[63] Continuation-in-part of Ser. No. 267,210, May 21, 1981, Pat. No. 4,355,032.

[51] Int. Cl.³ .............................................. A61K 31/52
[52] U.S. Cl. ................................... 424/253; 544/276; 544/277
[58] Field of Search ................ 544/276, 277; 424/253

[56] References Cited

U.S. PATENT DOCUMENTS

| | | | |
|---|---|---|---|
| 4,146,715 | 3/1979 | Schaeffer | 544/276 |
| 4,199,574 | 4/1980 | Schaeffer | 544/276 |
| 4,323,573 | 4/1982 | Schaeffer | 544/277 |
| 4,340,726 | 7/1982 | Simon et al. | 544/253 |
| 4,347,360 | 8/1982 | Ogilvie | 544/276 |
| 4,355,032 | 10/1982 | Verheyden et al. | 424/253 |

Primary Examiner—Nicholas S. Rizzo
Attorney, Agent, or Firm—Annette M. Moore; Tom M. Moran

[57] ABSTRACT

The compound 9-(1,3-dihydroxy-2-propoxymethyl)-guanine and the pharmaceutically acceptable salts thereof are useful as antiviral agents.

3 Claims, No Drawings

9-(1,3-DIHYDROXY-2-PROPOXYMETHYL)GUANINE AS ANTIVIRAL AGENT

This is a continuation-in-part of Ser. No. 267,210 filed May 21, 1981 now U.S. Pat. No. 4,355,032.

BACKGROUND OF THE INVENTION

1. Field of the Invention

This invention relates to a method of treating viral infections in warm blooded and cold blooded animals using 9-(1,3-dihydroxy-2-propoxymethyl)guanine and pharmaceutically acceptable salts thereof.

2. Related Disclosure

Viral infections are widespread and result in a wide variety of symptoms. Some viral infections are easily overcome by the body's defense mechanism while others are of a more serious nature leading to permanent damage, e.g., blindness, and even to death. One such family of viruses which may cause serious infections is the Herpes virus group.

The drugs presently used to treat viral infections are ineffective in many cases or, if effective, are needed in large and/or continuous dosages which produce serious side-effects and/or toxicity. Therefore there is a need for an effective antiviral agent which is effective at lower dosages than the presently available drugs, thus diminishing the chance of possible side-effects and toxicity.

U.S. Pat. No. 4,199,574 discloses compounds represented by the following generic formula:

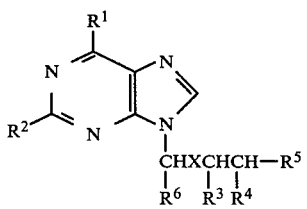

wherein X is sulphur or oxygen, $R^1$ is hydrogen, halogen, hydroxy, alkoxy, azide, thio, alkylthio, amino, alkylamino or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzyloxy, benzoyloxy, benzoyloxymethyl, sulphamoyloxy, phosphate, carboxypropiamyloxy, straight chain or cyclic acyloxy having from 1 to 8 carbon atoms e.g., acetoxy or substituted carbamoyl group of formula NHCO-Z wherein Z is alkyl, aryl or aralkyl optionally substituted by one or more of sulphonyl, amino, carbamoyl or halogen; $R^6$ is hydrogen or alkyl, provided that when X is oxygen and $R^2$, $R^3$, $R^4$, and $R^6$ are hydrogen, $R^1$ is not amino or methylamino when $R^5$ is hydrogen or hydroxy, or a salt thereof.

The class of compounds represented by the above formula and the pharmaceutically acceptable acid addition salts thereof are described to exhibit antiviral activity. See also *Tetrahedron Letters*, 21, 327-30 (1980).

SUMMARY OF THE INVENTION

It has now been discovered that, surprisingly, one specific compound, 9-(1,3-dihydroxy-2-propoxymethyl)guanine of the above class and its salts is a particularly active antiviral agent. The selective activity of this compound is highlighted when the compound is compared with the structurally most similar compounds disclosed in U.S. Pat. No. 4,199,574 in an antiviral assay as shown in detail in Example 5.

The present invention relates to a method of treating viral infections in warm blooded and cold blooded animals using the compound 9-(1,3-dihydroxy-2-propoxymethyl)guanine which may be represented by the formula

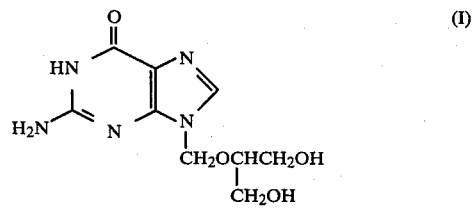

or the pharmaceutically acceptable salts thereof or a composition containing same as an active ingredient.

DETAILED DESCRIPTION AND PREFERRED EMBODIMENT

As used in the specification and appended claims, unless specified to the contrary, the following terms have the meaning indicated.

"Pharmaceutically acceptable salts" refers to those salts which possess the biological effectiveness and properties of the free compound and which are not biologically or otherwise undesirable. The salts may be either the acid addition salts or alkali metal salts. Suitable acids for salt formation are inorganic acids such as hydrochloric acid, hydrobromic acid, sulfuric acid, nitric acid, phosphoric acid and the like, and organic acids such as trifluoroacetic acid, menthanesulfonic acid, ethanesulfonic acid, p-toluenesulfonic acid and the like. Suitable bases for salt formation are alkali metal bases such as alkali metal hydroxides, e.g., sodium hydroxide, potassium hydroxide and the like.

The compound of the present invention characterized by formula (I) above, and the pharmaceutically acceptable salts thereof, are distinguished by the discovery that the 1,3-dihydroxy-2-propoxymethyl group substituted at the 9-position of the guanine nucleus provides, surprisingly, a highly active compound.

UTILITY AND ADMINISTRATION

The subject compound of formula (I) and the pharmaceutically acceptable salts thereof exhibit potent antiviral activity when administered to warm blooded and cold blooded animals, particularly mammals, birds, and fish, but most particularly humans. For example, the compound of the present invention exhibits excellent activity against Herpes Simplex virus I and II and related viruses such as cytomegalovirus, Epstein-Barr virus and varicella Zoster virus.

Pharmaceutical compositions, both veterinary and human, containing the subject compound appropriate for antiviral use are prepared by methods and contain excipients which are well known in the art. A generally recognized compendium of such methods and ingredients is *Remington's Pharmaceutical Sciences* by E. W. Martin, (Mark Publ. Co., 15th Ed., 1975).

The compound of the invention may be administered parenterally (for example, by intraveneous, subcutaneous, intraperitoneal or intramuscular injection), orally, topically or rectally.

The compositions are administered orally or parenterally at dose levels, calculated as the free base, of about 0.1 to 300 mg/kg, preferably 1.0 to 30 mg/kg of mammal body weight, and are used in man in a unit dosage form, administered one to five times daily in the amount of 1 to 500 mg per unit dose. For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated. The amount of compound of formula (I) in the formulation may vary from 0.1 percent weight (%w) to 99%w or more of the compound based on the total formulation and about 1%w to 99.9%w excipient. Preferably the compound is present at a level of 10%–95%w.

For parenteral administration or for administration as drops, as for eye infections, the compounds may be presented in aqueous solution in a concentration of from about 0.1 to 10%, more preferably about 0.1 to 7%. The solution may contain antioxidants, buffers, and other suitable additives.

Alternatively for infections of the eye, or other external tissues, e.g. mouth and skin, the compositions are preferably applied to the infected part of the body of the patient topically as an ointment, cream, aerosol or powder, preferably as an ointment or cream. The compounds may be presented in an ointment, for instance with a water soluble ointment base, or in a cream, for instance with an oil in water cream base, in a concentration of from about 0.01 to 10%; preferably 0.1 to 7%, most preferably about 3.0% w/v. Additionally, viral infections of the eye, such as Herpetic keratitis may be treated by use of a standard release drug delivery system as is described in U.S. Pat. No. 4,217,898.

The compounds of the present invention or compositions containing same are also useful in treating non-human mammals, birds, e.g., chickens and turkeys, and cold-blooded animals, e.g., fish. For example, the compounds of the present invention and compositions containing same exhibit antiviral activity against the following non-human viruses:

Sciruid herpesvirus 1
  Cavlid herpesvirus 1
  Lagomorph herpesvirus 1
  Phasianid herpesvirus 1
  Phasianid herpesvirus 2 (Marek's disease)
  Turkey herpesvirus 1
  Anatid herpesvirus 1
  Catfish herpesvirus 1
  Equid herpesvirus 3
  Bovid herpesvirus 1
  Bovid herpesvirus 2
  Bovid herpesvirus 3
  Bovid herpesvirus 4
  Pig herpesvirus 1
  Pig herpesvirus 2
  Murid herpesvirus 1
  Cebid herpesvirus 1
  Cebid herpesvirus 2
  Tupaiid herpesvirus 1
  Canine herpesvirus 1
  Feline herpesvirus 1
  Equid herpesvirus 1
  Equid herpesvirus 2

Avian viral diseases such as Marek's disease and the like are prevented and/or treated by compounds of the present invention by methods well-known in the veterinary art such as by injecting the birds with the composition containing the compound, or by adding the compound of the instant invention to feed or drinking water.

Fish which are in a confined area such as a pool, aquarium or holding tank may also be treated for viral infections such as herpeslike viruses, e.g., channel catfish virus (CCV), herpes-virus salomones, Nerka virus and the like by adding the compound directly to the water of the pool, aquarium or holding tank or by incorporating the compounds into the feed.

The exact regimen for administration of the compounds and compositions disclosed herein will necessarily be dependent upon the needs of the individual subject being treated, the type of treatment and, of course, the judgement of the attending practitioner.

PREPARATION

The compound of formula (I) may be prepared by the following reaction scheme.

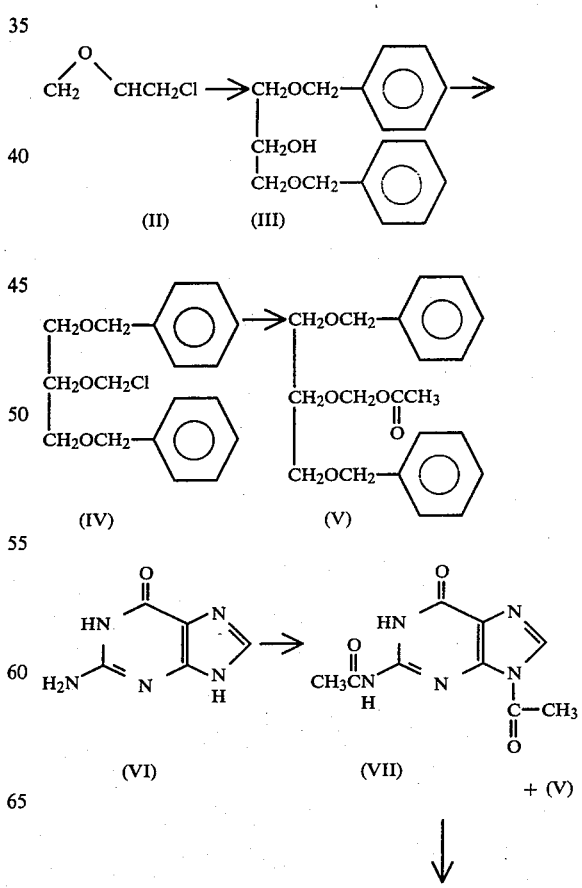

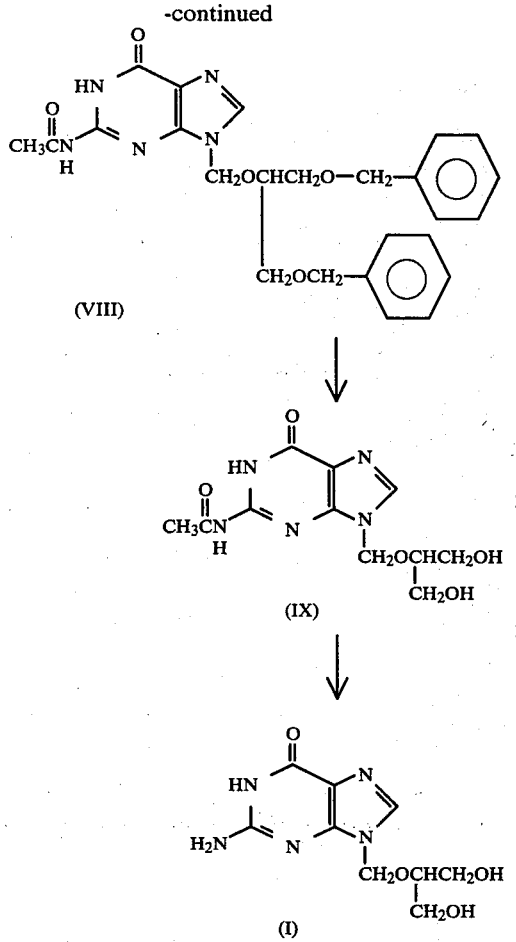

The compound of formula (III) is prepared by adding epichlorohydrin (II) dropwise to a solution of an alkali metal salt, preferably the sodium salt, of optionally substituted benzyl alcohol in a solvent such as dimethylformamide, dimethylacetamide, hexamethylphosphoramide, dimethylsulfoxide, sulfolane, tetrahydrofuran, and dioxane at a temperature of about 0° C. to 100° C., preferably at about 15° C. to 40° C. The reaction mixture is stirred from about 10 hours to 24 hours, preferably from about 12 hours to 18 hours at a temperature of about 0° C. to 100° C., preferably from about 20° C. to 50° C.

Compound of formula (III) is chloromethylated to compound of formula (IV) by bubbling dry hydrogen chloride gas in a solution of the compound and paraformaldehyde dissolved in a halogenated hydrocarbon solvent such as dichloroethane, chloroform, dichloromethane, and 1,1,2-trichloroethane cooled to a temperature of about 0° C. to 25° C., preferably at a temperature of about 0° C. The hydrogen chloride gas is added over 30 minutes to 3 hours, preferably over 1 hour to 2 hours until the paraformaldehyde dissolves. The solution is held at a temperature from about 0° C. to 10° C. for about 12 hours to 48 hours, preferably from about 0° to 5° for about 16 hours to 24 hours.

Compound of formula (V) is prepared by reacting an alkali metal acetate such as sodium acetate with compound of formula (IV) dissolved in a solvent such as dimethylformamide, tetrahydrofuran, dimethylacetamide, hexamethylphosphoramide, dimethylsulfoxide, sulfolane, and dioxane at a temperature of about 0° C. to 45° C., preferably from about 0° C. to 25° C. The solution is stirred from about 5 to about 24 hours, preferably from about 10 hours to about 18 hours at a temperature of about 10° C. to about 30° C., preferably at a temperature of about 15° C. to 25° C.

Compound of formula (VII) is prepared by heating guanine (VI) with acetic anhydride, neat, at reflux for about 10 to 24 hours, preferably for about 12 to 18 hours.

$N^2$,9-Diacetylguanine of formula (VII) is reacted with compound of formula (V) to form compound of formula (VIII) neat or in a solvent such as dioxane, sulfolane and the like in the presence of a catalytic amount of an acid such as bis(p-nitrophenyl)phosphate, toluene sulfonic acid, methylphosphonic acid or dichloroacetic acid, preferably bis(p-nitrophenyl)phosphate at a temperature of about 75° C. to 200° C., preferably at about 110° C. to 180° C. The reaction is generally carried out using 0.8 moles to 1.2 moles of compound of formula (V) to one mole of compound of formula (VII).

The benzyl protecting groups are removed from compound of formula (VIII) by catalytic hydrogenation to form compound of formula (IX). A catalyst such as palladium on carbon in a slurry is added to a solution of compound of formula (VIII) dissolved in a solvent such as aqueous methanol. Hydrogen is added to the solution at a pressure of 15 psi to 200 psi, preferably at a pressure of 30 psi to 80 psi.

Compound of formula (I) is prepared by deacetylating compound of formula (IX) with a base such as ammonia dissolved in an alcohol such as methanol. A solution of compound of formula (IX) and the base is stirred for about 5 hours to 36 hours, preferably for about 10 hours to 24 hours at a temperature of about 10° C. to 30° C., preferably at a temperature of about 15° C. to 25° C.

The following specific description is given to enable those skilled in the art to more clearly understand and practice the invention. It should not be considered as a limitation upon the scope of the invention but merely as being illustrative and representative thereof.

PREPARATION I

Preparation of 1,3-Di-O-benzylglycerol

Sodium hydride (100 g (50% dispersion in mineral oil), 2.08 mol) was washed twice with 1 l of hexane then dried under nitrogen. Dry dimethylformamide (1.5 l) was added. Benzyl alcohol (400 ml) was then added at such a rate to keep the temperature below 50° C. The addition took 2 hours. Epichlorohydrin (92.5 g, 1 mol) was then added dropwise over 0.5 hour with ice cooling in order to keep the temperature below 40° C. The solution was next stirred for 16 hours at 21° C. then for 2.5 hours at 50° C. The dimethylformamide was then removed by evaporation at reduced pressure. The oily residue was dissolved in 2.5 l diethyl ether. The organic solution was washed with 2 l of water, 2 l of 2% hydrochloric acid, 2 l of 1% sodium bicarbonate, and 1 l of brine, dried over sodium sulfate, and concentrated to a brown oil. Distillation gave 147.8 g of 1,3-di-O-benzylglycerol (bp 170°–180° C./1 torr).

PREPARATION II

Preparation of 1,3-Di-O-benzyl-2-O-chloromethylglycerol

Dry hydrogen chloride gas was bubbled for 1.5 hours into a solution of 1,3-di-O-benzylglycerol from Preparation I (15 g, 55 mmol) and paraformaldehyde (3.3 g, 110 mmol) in 175 ml of 1,2-dichloroethane at 0° C. The solution was then stored in a stoppered flask for 21 hours at 4° C. Next, the solution was dried over magnesium sulfate with warming to 21° C. then filtered and concentrated to give 17.5 g of 1,3-di-O-benzyl-2-O-chloromethylglycerol.

PREPARATION III

Preparation of 2-O-Acetoxymethyl-1,3-di-O-benzylglycerol

To a solution of 1,3-di-O-benzyl-2-O-chloromethylglycerol from Preparation II (17.5 g, 55 mmol) in 400 ml of dimethylformamide at 0° C. under a drying tube was added sodium acetate (6 g). The solution was then warmed to 21° C. and magnetically stirred for 15 hours. The solvent was removed by evaporation at reduced pressure and the oily residue dissolved in 1 pound of diethylether. The ether solution was washed once with 750 ml of water, two times with 250 ml of water, and once with 250 ml of brine, dried over sodium sulfate and concentrated to give 19 g of 2-O-acetoxymethyl-1,3-di-O-benzylglycerol as an oil.

PREPARATION IV

Preparation of $N^2$,9-Diacetylguanine

Guanine (20 g, 0.132 mol) was combined with 300 ml of acetic anhydride and the mixture heated at reflux for 16 hours. The mixture was cooled and the excess acetic anhydride removed by evaporation at reduced pressure. The residue was recrystallized from dimethyl sulfoxide to give 25.6 g of $N^2$,9-diacetylguanine.

EXAMPLE 1

(A) Preparation of $N^2$-Acetyl-9-(1,3-dibenzyloxy-2-propoxymethyl)guanine $N^2$,9-Diacetylguanine from Preparation IV (15.61 g, 66 mmol), 2-O-acetoxymethyl-1,3-di-O-benzylglycerol from Preparation III (19 g, 55 mmol), and bis(p-nitrophenyl)phosphate (0.5 g) were stirred together with 150 ml of diethylether. The solvent was removed by evaporation and the residue heated in a 175° C. oil bath for 1.5 hours under a stream of nitrogen. Column chromatography eluting with 1:9 methanol/methylene chloride followed by recrystallization from ethyl acetate afforded 4.76 g of $N^2$-acetyl-9-(1,3-dibenzyloxy-2-propoxymethyl)guanine, mp 145°–146° C.

(B) Preparation of $N^2$-Acetyl-9-(1,3-dihydroxy-2-propoxymethyl)guanine

To a solution of $N^2$-acetyl-9-(1,3-dibenzyloxy-2-propoxymethyl)guanine (4.62 g, 9.67 mmol) in 150 ml of methanol plus 40 ml of water was added 20% palladium hydroxide on carbon as a slurry in 10 ml of water. The mixture was hydrogenated on a Parr hydrogenator at 60 psi of hydrogen for 38 hours then filtered through celite and concentrated to a white solid. Recrystallization from methanol/ethyl acetate gave 1.4 g of $N^2$-acetyl-9-(1,3-dihydroxy-2-propoxymethyl)guanine, mp 205°–208° C.

The mother liquor was further reduced with 10% palladium on carbon (1 g) in 150 ml of methanol plus 50 ml of water at 60 psi for 47 hours. The total yield of $N^2$-acetyl-9-(1,3-dihydroxy-2-propoxymethyl)guanine was 2.11 g.

(C) Preparation of 9-(1,3-Dihydroxy-2-propoxymethyl)guanine $N^2$-Acetyl-9-(1,3-dihydroxy-2-propoxymethyl)guanine (721.9 mg, 2.4 mmol) was stirred with 50 ml of methanolic ammonia solution (methanol saturated with ammonia at 0° C.) for 17 hours at 21° C. The solution was concentrated to a white solid and the residue recrystallized from methanol to give 582.3 mg of 9-(1,3-dihydroxy-2-propoxymethyl)guanine, mp 250° C. d.

EXAMPLE 2

9-(1,3-Dihydroxy-2-propoxymethyl)guanine was dissolved in a solution of water containing one mole equivalent of sodium hydroxide. The solution was then lyophilized to give 9-(1,3-dihydroxy-2-propoxymethyl)guanine sodium salt as a white powder.

EXAMPLE 3

The sodium salt of 9-(1,3-dihydroxy-2-propoxymethyl)guanine was dissolved in a minimum amount of water and dilute hydrochloric acid was added to adjust the pH to 7. 9-(1,3-Dihydroxy-2-propoxymethyl)guanine, m.p. 250° C. d crystallized from the solution.

EXAMPLE 4

The following example illustrates the preparation of representative pharmaceutical formulations containing an active compound of Formula (I).

| A. Topical Formulation | |
|---|---|
| Active compound | 0.2–2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water qs | 100 ml |

All of the above ingredients, except water, are combined and heated at 60° C. with stirring. A sufficient quantity of water at 60° C. is then added with vigorous stirring to provide 100 g of the cream formulation which is then cooled to room temperature.

The following formulation is useful for intraperitoneal and intramuscular injection.

| B. IP and IM Formulation | |
|---|---|
| Active compound | 0.5 g |
| Propylene glycol | 20 g |
| Polyethylene glycol | 20 g |
| Tween 80 | 1 g |
| 0.9% Saline solution qs | 100 ml |

The active compound is dissolved in propylene glycol, polyethylene glycol 400 and Tween 80. A sufficient quantity of 0.9% saline solution is then added with stirring to provide 100 ml of the I.P. or I.M. solution which is filtered through a 0.2 micron membrane filter and packaged under sterile conditions.

The following formulation is useful for intravenous injection.

| C. I.V. Formulation | |
|---|---|
| Active compound | 0.5 g |

| -continued |
|---|
| C. I.V. Formulation |
| 0.9% Saline solution 100 g |

The active compound is added to 100 ml of 0.9% saline solution with stirring to provide 100 ml of I.V. solution which is filtered through a 0.2 micron membrane filter and packaged under sterile conditions.

| D. Tablet Formulation | |
|---|---|
| | Parts by weight |
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active compound) with an appropriate tabletting machine.

EXAMPLE 5

The exceptional antiviral activity of the compound of the invention is illustrated by the following assay procedures:

The Herpes simplex virus 2 strain G for infection was prepared in HEp-2 cell cultures. Virus was adsorbed for 1 hour, fresh media was placed on the cells, and they were incubated at 35° C. until all cells were infected. The cell suspension was frozen at −70° C., thawed, and centrifuged to remove cell debris. The supernatant fluid was aliquoted and stored frozen at −70° C. until use. A $10^{6.7}$ dilution of the supernatant fluid produced a 50% cell culture infective dose ($CCID_{50}$) in HEp-2 cells and a $10^{3.7}$ dilution produced a 50% lethal challenge ($LC_{50}$) in mice.

Groups of 20 Swiss Webster female mice (15–17 gm), were challenged by intraperitoneal route using 0.2 ml of EMEM containing 10 $LC_{50}$/mouse of virus. Mice challenged with $10^{0.5}$ more or less virus than the 10 $LD_{50}$ challenge served as a virulence control to assure the model was working properly.

Treatment with test compounds began 6 hours post-challenge. The mice, divided into groups of 20, were administered the compounds in saline s.c. at 5 mg/kg, 10 mg/kg and 20 mg/kg. One group of 20 mice was used as a control group and administered saline s.c. The treatment was repeated at 24, 48, 72 and 96 hours post-challenge.

Test compounds were the compound of the invention, and three compounds disclosed in U.S. Pat. No. 4,199,574 having structural similarity to portions of the compound of the invention.

| Test Compound | Dosage | Survivors (out of 20) Days Post Challenge | | |
|---|---|---|---|---|
| | | 12 | 14 | 21 |
| Untreated Controls | | 0 | 0 | 0 |
| 9-(1,3-dibenzoxy-2-propoxy methyl)adenine | 5 mg/kg | 2 | 2 | 2 |
| | 10 mg/kg | 1 | 0 | 0 |
| | 20 mg/kg | 1 | 1 | 1 |
| 9-(1,3-dibenzoxy-2-propoxy methyl)-6-mercaptopurine | 5 mg/kg | 2 | 0 | 0 |
| | 10 mg/kg | 0 | 0 | 0 |
| | 20 mg/kg | 1 | 0 | 0 |
| 9-(1-hydroxy-2-ethoxy methyl)guanine | 5 mg/kg | 1 | 1 | 1 |
| | 10 mg/kg | 3 | 3 | 3 |
| | 20 mg/kg | 5 | 4 | 4 |
| 9-(1,3-dihydroxy-2-propoxy methyl)guanine | 5 mg/kg | 15 | 14 | 14 |
| | 10 mg/kg | 19 | 18 | 18 |
| | 20 mg/kg | 19 | 18 | 15 |

In the above results, a comparison between the number of surviving animals administered the compound of the invention and the number of surviving animals administered the three prior art compounds clearly demonstrates the markedly superior antiviral activity of our compound.

What is claimed is:

1. Method of treating viral infections in a warm blooded or a cold blooded animal having a viral infection which comprises administering an effective amount of 9-(1,3-dihydroxy-2-propoxymethyl)guanine or a pharmaceutically acceptable salt thereof or a composition containing same as an active ingredient.

2. Method according to claim 1 of treating a warm blooded animal.

3. Method according to claim 1 of treating a cold blooded animal.

* * * * *